United States Patent [19]

Schimmel

[11] Patent Number: 4,963,487
[45] Date of Patent: * Oct. 16, 1990

[54] METHOD FOR DELETION OF A GENE FROM A BACTERIA

[75] Inventor: Paul R. Schimmel, Lexington, Mass.

[73] Assignee: Massachusetts Institute of Technology, Cambridge, Mass.

[*] Notice: The portion of the term of this patent subsequent to Dec. 15, 2004 has been disclaimed.

[21] Appl. No.: 96,958

[22] Filed: Sep. 14, 1987

Related U.S. Application Data

[63] Continuation-in-part of Ser. No. 688,612, Jan. 3, 1985, Pat. No. 4,713,337, and a continuation-in-part of Ser. No. 833,920, Feb. 26, 1986, Pat. No. 4,774,180.

[51] Int. Cl.$^5$ ............... C12N 15/00; C12N 7/00; C07H 15/12
[52] U.S. Cl. ............... 435/172.3; 435/172.1; 435/320; 435/849; 536/27; 935/29; 935/73; 935/83; 935/84
[58] Field of Search ............... 435/172.1, 172.3; 536/27; 935/10, 9, 11

[56] References Cited

PUBLICATIONS

Gutterson et al., *Proc. Natl. Acad. Sci., U.S.A.*, 80:4894–4898, (1983).
Lee et al., *J. Bacteriol.*, 153:685–692, (1983).
Rothstein, In *Methods in Enzymology*, 101:202–211, (1983).
Clark et al., *Ann. Rev. Genetics*, 7:67–86, (1974).
N. Kleckner, *J. Mol. Biol.*, 116, 125–159, (1977).
Scherer et al., *Proc. Natl. Acad. Sci., U.S.A.*, 76(10), 4951–4955, (Oct. 1979).
P. J. Goldmark et al., *J. of Biol. Chem.*, 247(6), 1849–1860, (1972).
A. Sancar et al., *Proc. Natl. Acad. Sci.*, 77(5), 2611–2615, (May, 1980).
T. Horii et al., *Proc. Natl. Acad. Sci.*, 77(1), 313–317, (Jan., 1980).
J. H. Miller, *Experiments in Molecular Genetics*, 196–200, (Cold Spring Harbor Laboratory, 1972).

*Primary Examiner*—Thomas D. Mays
*Attorney, Agent, or Firm*—Kilpatrick & Cody

[57] ABSTRACT

Disclosed is a method and linear DNA fragments for use in the deletion of a gene from a bacteria with a single step procedure that is applicable to any essential or nonessential gene which has been cloned. Chromosomal deletions are constructed by transformation of a cell strain with linear DNA fragments containing a locus for resistance to an antibiotic, or any other gene allowing for rapid phenotypic selection, flanked by sequences homologous to closely spaced regions on the cell chromosome on either side of the gene to be deleted, in combination with the immediate subsequent deletion or inactivation of the recA gene. By selecting for a double-crossover event between the homologous sequences, shown by the antibiotic resistance or other detectable phenotype, a chromosome disruption can be selected for which has effectively deleted an entire gene. Inactivation or deletion of the recA gene prevents recombination or incorporation of extrachromosomal elements from occurring, thereby resulting in a bacterial strain which is useful for screening for functional activity or production of genetically engineered proteins in the absence of specific contaminants.

10 Claims, No Drawings

METHOD FOR DELETION OF A GENE FROM A BACTERIA

The Government has rights in this invention pursuant to Grant Number NIH-5-R01-GM-23562 awarded by the Department of Health & Human Services.

BACKGROUND OF THE INVENTION

This is a continuation-in-part to U.S. Ser. No. 688,612, entitled "A Method for Deletion of a Gene From a Bacteria" filed Jan. 3, 1985 by Maria Jasin and Paul R. Schimmel issued Dec. 15, 1987 as U.S. Pat. No. 4,713,337 and U.S. Ser. No. 833,920 now U.S. Pat. No. 4,774,180 entitled "Construction and Application of Polyproteins" filed Feb. 26, 2986 by Matthew J. Toth and Paul R. Schimmel This invention relates to a method and means for deleting a gene from a bacterial chromosome in a single step.

Many applications require the construction of special bacterial strains which have a particular genetic background. These genetic backgrounds are the framework in which specific recombinant DNA plasmid constructions are tested to determine whether they can provide functions which are missing from the background of the bacteria. If such functions are provided by the recombinant plasmid, then there is positive evidence that a particular genetic locus or loci is encoded by the plasmid. The construction of genetic backgrounds is therefore a vital step in the subsequent cloning and investigation of specific genes.

The most common backgrounds are those in which a single mutation is present in a specific gene on the bacterial chromosome. This may result in synthesis of a defective version of the protein encoded by that gene, resulting in a specific cellular dysfunction. Correction of the cellular dysfunction, by introduction of a specific recombinant plasmid, is evidence that the relevant gene has been cloned onto the specific plasmid However, a mutant protein may not be silent and may undergo interactions with other components, thereby creating the appearance that the plasmid gene encodes the entire active protein when it does not. This can seriously confuse the analysis. A much less ambiguous and therefore more desirable approach is one in which the gene in question has been deleted. In these circumstances, there is no production whatsoever of a mutant protein.

Another situation where it is desirable to delete a complete gene from the chromosome of a bacteria is when the bacteria is being used in the production of a genetically engineered protein. Examples of these situations include the expression of insulin, growth hormone, protein A, and various vaccines from recombinant genes inserted into *E. coli*. Many times the *E. coli* produces proteins which contaminate the purified product produced by the genetic engineering. Although it is possible to add additional purification steps to remove this contaminant, it would be preferable to avoid the problem entirely by deleting the gene encoding the contaminating protein Methods that are presently used to alter a gene include random mutation or inactivation of the gene sequence by mutation, insertion, or deletion of some portion of the gene. However, this can still lead to the production of inactive protein fragments or deletion of more of the chromosome than is necessary or desirable.

It is therefore an object of the present invention to provide a method and means for deleting a specific gene from a bacteria.

It is another object of the present invention to provide a method and means for inserting and/or inactivating or deleting the recA gene in a variety of bacteria.

SUMMARY OF THE INVENTION

Disclosed is a method for the deletion of a gene from a bacteria using a single step procedure that is applicable to any gene that has been cloned. The procedure depends upon site-directed recombination of linear DNA fragments with sequences on the chromosome as a function of recA in combination with the subsequent inactivation or deletion of the recA gene.

The basic strategy for construction of chromosomal deletions is to transform the bacteria with linear DNA fragments which contain an antibiotic resistant or other phenotypically detectable gene segment (a "marker") flanked by sequences homologous to a closely spaced region on the cell chromosome containing the gene to be deleted A double-crossover event within the homologous sequences, effectively deleting the entire gene, is selected for by screening for the antibiotic resistant phenotype.

The linear fragment is not integrated into the chromosome in the absence of enzymes expressed by the recA gene. Accordingly, if the gene is absent or inactive, a recA gene must be inserted into the cell prior to the linear recombination event, and then inactivated or removed to prevent subsequent incorporation of other non-chromosomal sequences into the chromosome. This is particularly important if the bacteria is used as a host for the expression of genetically engineered proteins from sequences carried on plasmids or other extrachromosomal elements. The recA gene can be provided either in the form of an extrachromosomal element such as a plasmid or through incorporation of the gene into the chromosome. The recA gene is preferably inactivated or deleted by means of a double reciprocal recombination event utilizing linear sequences containing sequences homologous to the flanking sequences on either side of the recA gene in the chromosome. This is essentially the same method used to delete or insert a gene into the chromosome by homologous recombination as described above.

The present invention includes isolated linear DNA fragments constructed for use in the method for deleting a gene from the chromosome and for inserting or deleting the recA gene.

The method and sequences are applicable to a variety of bacteria including strains of Escherichia, Pseudomonas, Agrobacterium, Proteus, Erwinia, Shigella, Bacillus, Rhizobium, Vibrio, Salmonella, Streptococcus, and Haemophilus.

DETAILED DESCRIPTION OF THE INVENTION

The present invention is a method for deleting any gene from a bacterial strain employing linear DNA fragments incorporating sequences homologous to the sequences flanking the gene to be deleted in the chromosome and sequences allowing insertion or removal/inactivation of recA in a variety of bacteria.

Homologous recombination has been detected in a wide variety of organisms, from simple bacteriophages to complex eucaryotic cells. Genetic and biochemical investigations have defined roles for several enzymes needed in recombination. The RecA protein participates in the early steps of synapse, allowing alignment of DNA molecules before exchange, in strand transfer, where there is transfer of a single-stranded segment to a recipient duplex to form a limited heteroduplex region between the interacting DNAs and in the extension of this heteroduplex region by a reaction involving the concerted winding and unwinding of incoming and outgoing DNA chains, respectively. The hydrolysis of ATP by RecA protein is required for these events in vitro.

The recA gene performs another equally important role in cell metabolism by controlling expression of a group of unlinked genes that aid in recovery of cells after exposure to DNA-damaging agents. This response, termed the SOS response, involves genes that participate in repair of DNA damage, mutoganesis, and coordination of cell division events.

The purified RecA protein is a single polypeptide ranging in weight from about 37,000 to about 42,000. Although there is some variation in the sequences between bacterial strains, the recA proteins from a variety of bacteria in general have been isolated and characterized by interspecies complementation and assays utilizing comparisons with isolated, characterized proteins.

The present method and the linear fragments for use in the present method are not limited to organisms such as *E. coli*. The recA gene is found in a variety of bacteria including both gram negative and gram positive organisms. The recA gene has been isolated or identified and characterized in several organisms. It is possible to prepare a genomic library from any bacterial species and to isolate a clone containing a sequence homologous to a characterized recA gene by interspecific complementation using one of the available DNA clones containing a recA sequence or cross-reactivity with antisera to RecA proteins from a well-characterized organism such as *E. coli*.

RecA+ and RecA− strains are available from a variety of sources. For example, cloning and characterization of recA genes and recA proteins from *Proteus vulgaris, Erwinia carotovoria, Shigella flexneria* and *Escherichia coli* are described by S. L. Keener, et al., in *J. Bacter.* 160(1), 153–160 (1984). The RecA proteins produced by these organisms were demonstrated to be highly conserved among the species. In fact, the protein produced by one species could be introduced into another species where it complemented repair and regulatory defects of recA mutations. Other bacterial recA genes and gene products have been described by C.A. Miles, et al, in *Mol. Gen.Genet.* 204,161–165 (1986) *(Agrobacterium tumefaciens* C58), I. Goldberg et al, *J. Bacteriol.* 165(3), 715–722(1986), (*Vibrio cholera*), M. Better et al, *J. Bacteriol.* 155(1), 311–316 (1983), (*Rhizobium meliloti*), T.A. Kokjohn et al, *J. Bacteriol.* 163(2), 568–572 (1985), (*Pseudomonas aeruginosa*), and C.M. Lovett, Jr. et al, *J. Bio.Chem.* 260(6), 3305–3313 (1985) (*Bacillus subtilis*). These articles detail the isolation and characterization of gene libraries and the proteins encoded by the recA genes using techniques known to those skilled in the art including construction of gene libraries, identification of homologous genes using hybridization to probes from other more well characterized species such as *E. coli*, isolation and characterization of RecA proteins using antisera to RecA proteins from *E. coli*, and interspecies complementation of deficient strains of *E. coli* using gene segments from the libraries. The isolated proteins were useful for in vitro complementation studies. Rec A deficient strains and RecA clones are available from many of the laboratories cited in the above articles and from the *E. coli* Genetic Stock Center at Yale University run by Dr. Barbara Bachman.

The method whereby the DNA fragment is introduced into the chromosome to delete a gene or to regulate recA involves the construction of linear DNA fragments which have sequences homologous to closely spaced regions on the chromosome in the bacteria which flank each side of the gene of interest. In general, they must contain at least 80 to 100 nucleotides homologous to sequences flanking the gene to be deleted or the recA gene. An antibiotic resistant locus such as Kan[r], which encodes a protein making the bacterial resistant to the antibiotic, or other marker, is placed between these flanking sequences.

The linear DNA segment is introduced into a specific cell strain and selection is done for a double, reciprocal recombination which will delete the target gene and insert the marker into its place. As a result of the insertion of the antibiotic resistant gene, the cells are now resistant to the antibiotic. Cells which do not contain the insertion are eliminated by growing the bacteria in a medium containing the antibiotic.

Any other gene which allows for rapid screening of the cells containing a double, reciprocal recombination may be used in place of a gene for antibiotic resistance. For example, any gene for an essential protein, including enzymes, cofactors, proteins which are necessary for the synthesis of essential lipids, polysaccharides, nucleic acids, and other protein molecules such as receptors, as well as nucleic acids which have functional activity such as ribozymes, may be used. Other genes which confer a detectable phenotype on the cell strain such as sensitivity to temperature or ultraviolet radiation, auxotrophism for a sugar, amino acid, protein or nucleotide, or any other phenotype which can be detected by chemical indicators either in vitro or in vivo assay, or an immunoassay for a specific cellular component may also be used. Such chemical, radioactive, or immunological screening assays are well known to those skilled in the art.

In one application, in which the goal is to produce and purify a foreign protein, and the microorganism encodes its own version of the protein, the gene for the microorganism's own protein is eliminated. The gene for the foreign protein is then inserted and the protein produced. The purification process is thereby simplified since there is no contamination by the host protein, whether analogous to the protein being produced or unrelated which copurifies with, or interefers with the purification of, the protein being produced. For example, a protein may interfer with binding of the protein to be purified to a column.

In a second application, a plasmid is used to introduce a gene into an organism which typically contains a mutation in the gene to be investigated resulting in a negative phenotype for the product of the gene to be investigated. Failure of the organism to produce a biologically active form of the protein encoded by the mutated gene may confer a lethal phenotype under certain defined conditions. For example, this can be at a temperature, designated as the restrictive temperature, at which the mutant protein denatures or otherwise undergoes inactivation. The cloned gene which is introduced is selected for by virtue of its ability to confer cell viability or any other detectable phenotype for the desired protein at the restrictive temperature. The acquisition of viability or other detectable phenotype at the normally restrictive temperature is evidence that the gene of interest has been cloned.

The major problem with this second system is that, unless the inactive gene is deleted in entirety, the defective host protein may interact with a protein produced from the introduced plasmid. This interaction may stabilize the defective host protein enough so that its activity is restored even at the restrictive temperature. In this case, the restoration of growth at the restrictive temperature would be a false positive, that is, the growth would not be due to activity encoded by the cloned DNA segment. This problem holds true for all selections based on complementation of a phenotype which is due to a defect in a specific protein. Such phenotypes include temperature sensitivity, amino acid auxotrophies or any other auxotrophies which result from a lack of synthesis of a key ingredient such as a sugar, nucleotide, critical protein or nucleic acid, or cofactor used for oxidation, reduction, or transamination reactions.

The problem of "false positives" also exists for cloned DNA pieces which are created to encode enzyme fragments as a means to define the catalytic core or to define any segment which achieves a specific purpose, such as a piece which undergoes self-association, binds to a specific ligand or receptor, or forms a specific complex or array with one or more additional components. In these cases, the engineering of protein fragments, which are tested in a host cell that encodes a defective version of the protein of interest, is seriously hampered if the defective host protein interacts in any way with the engineered pieces.

In the present invention, specifically designed linear DNA fragments are used to create a deletion of a gene by site-specific recombination. These fragments are transformed into the host cell. Cell viability or the detectable phenotype can be maintained during the procedure by provision of the gene encoding the desired protein on a recombinant plasmid that has a temperature-sensitive replicon, so that the cells which contain the deletion have a temperature sensitive phenotype. To achieve the deletion by recombination with the linear DNA fragments, it is necessary for the cells to have a RecA+ phenotype which is derived from recA, or its equivalent. Once recombination has occurred, the cell must immediately be changed to RecAo or else the temperature sensitive plasmid will recombine with homologous sequences on the chromosome. The same would apply to any other extrachromosomal element where integration into the host chromosome would be undesirable.

The RecA− phenotype may be achieved by simultaneous inactivation of recA during the transformation with linear fragments or, after the transformation, by immediately introducing RecA− by mating with an appropriate RecA− strain or by transduction with a phage which carries a RecA− gene segment. Although mutagenesis may also be an effective means of making the cell RecA−, this is a "hit or miss" approach. The preferred method is to use homologous recombination of linear DNA sequences bounded by sequences hybridizing to the sequences flanking the recA gene. The recA gene is necessary in order for the gene encoding the desired protein to be incorporated into the organism. However, any plasmids or other extrachromosomal elements in the cell will be incorporated unless the recA gene is immediately removed. This is a particular concern where the bacteria serves as a host for the expression of a genetically engineered protein from multicopy plasmids.

An example of the present invention, wherein linear DNA fragments were constructed which contained sequences homologous to those flanking the gene for $E.$ $coli$ alanyl tRNA synthetase and a Kan$^r$ locus inserted between these sequences, was described in U.S. Ser. No. 688,612 filed Jan. 3, 1985 entitled "A Method for Deletion of A Gene from a Bacteria" by Maria Jasin and Paul R. Schimmel. Selection was made for acquisition of resistance to the antibiotic, Kanamycin. As few as 240 base pairs were needed to achieve the second crossover. Cell viability was maintained by a temperature-sensitive plasmid which encodes alanyl tRNA synthetase. Candidates from this selection were characterized further. Proof of the predicted deletion was accomplished by DNA blot hybridization. The resulting cell strain does not contain the gene for an essential gene, alanyl tRNA synthetase, but can be maintained by means of a plasmid having a temperature sensitive replicon which encodes alanyl tRNA synthetase. When it becomes desirable to remove the plasmid, the bacteria are grown at the restrictive temperature. It is then possible to test alanyl tRNA synthetase gene fragments in the deficient strain to determine whether the fragments provide the function missing from the chromosome.

EXAMPLE OF SIMULTANEOUS DELETION/INACTIVATION OF recA AND THE GENE TO BE DELETED BY DOUBLE RECIPROCAL RECOMBINATION.

In the example in U.S. Ser. No. 688,612 filed Jan. 3, 1985, transformations were done into $E.$ $coli$ strain JC7623, which carries the recBC and sbcB mutant alleles. The recBC and sbcB mutations inactivate exonucleases which degrade linear DNA fragments, as described by P. J. Goldmark & S. Linn, *J. Biol. Chem* 247:1849–1860 (1972) and S.R. Kushner et al, *Proc. Natl. Acad. Sci. U.S.A.* 68:824 827 (1971). The sbcB mutation also suppresses the Rec− phenotype of recBC cells, so that homologous recombination functions via an alternative pathway. Because alaS is an essential gene, transformations were done into JC7623(pMJ901). Plasmid pMJ901 has a temperature-sensitive replicon and a wild-type allele of alaS. This plasmid maintains cell viability when the chromosomal copy of alaS has been deleted, but the resulting cells have temperature-sensitive phenotype.

In a recA+ background or its equivalent, integration of plasmid pMJ901 can occur through homologous recombination at residual alaS sequences on the interrupted chromosome. Because recA is adjacent to alaS on the chromosome, as disclosed by B.J. Bachman, *Microbiol. Rev.* 44:1–56(1980), it was possible to design linear DNA fragments which, when transformed into $E.$ $coli,$ simultaneously deleted a portion of recA and greater than 90% of alaS.

Two deletions, (ΔalaS1) and (ΔalaS2) were constructed from DNA fragments encoding an N-terminal fragment of the recA protein and a C-terminal segment of the alaS protein. For each linear DNA fragment, the recA segment and its flanking 5′ sequences are about 1.5 kb pairs; homologous recombination at these sequences destroys the carboxy-terminal coding region of recA protein, thereby inactivating it. The alaS sequences associated with the linear fragment are 1,100 bp (Δa- laS1) and 225 bp (ΔalaS2). The (ΔalaS1) deletion effectively removes the amino-terminal on-third of the 2,625 bp alaS coding region. All but the carboxy terminal 225 nucleotides are removed in the ΔalaS2 deletion.

Linear DNA fragments were derived from PvuI-BamHI-cut plasmid pMJ520 (ΔalaS1) and BamHI-cleaved pMJ525 (alaS2). Cells transformed with the linear DNA fragments were first selected for Kan$^r$; these transformants were then screened for the Amp$^S$ and UV and temperature-sensitive phenotypes.

The organization of sequences in strains containing the alaS1 and alaS2 alleles was examined by Southern blot hybridizations. The controls were the parental strains JC7623 and JC7623(pMJ901). A 1.8 kb BamHI-EcoRI hybridization probe was used to differentiate between the various gene arrangements. This probe contains a portion of recA and flanking 5' sequences, and is described by A. Sancar et al in *Proc. Natl. Acad. Sci. U.S.A.*, 76:3144-3148 (1979).

A PstI digest of chromosomal DNA from each of the four strains shows a 7.8 kb band which corresponds to the 5' end of recA, together with several kilobases of upstream sequences; this region is undisturbed in all cases. For JC7623 and JC7623(pMJ901) a 3.5 kb fragment also hybridizes to the probe. This corresponds to the PstI fragment which extends from an internal site within recA to a site within the carboxyl-terminal coding portion of alaS. For the two deletions, this band is missing and is replaced by a 1.1 kb fragment which extends from the internal PstI site within recA to the downstream PstI site in the Kan$^r$ gene.

Deletion of the single chromosomal copy of alaS enables rigorous testing for complementation of gene fragments that encode pieces of the deleted alanyl tRNA synthetase encoding gene. The gene fragments can be introduced via transformation of a pBR322-derived multicopy plasmid, or other vector. Only where the gene deletion removes all of the gene encoding proteins capable of complementing pieces of the protein to restore activity does one have a system that can be used to accurately measure the functional activity of a gene sequence.

EXAMPLE OF SUBSEQUENT DELETION AND/OR INACTIVATION OF recA FOLLOWING DELECTION OF A PROTEIN ENCODING GENE The glyS locus was deleted from *E. Coli* using a procedure based upon site specific recombination with a linear DNA fragment that replaces the target gene, in this case glyS, with a Kan$^r$ marker that is bounded by glyS 5' and 3' adjoining sequences. This recombination is done in *E. coli* JC7623 (recBC sbcB) where recBC sbcB mutations inactivate exonucleases that degrade linear DNA fragments. When the chromosomal copy of glyS is deleted to give the ΔglyS strain TM101, cell viability is maintained with plasmid pMT 901. Plasmid pMI 901 encodes a HindIII fragment that contains glyS cloned into the HindIII site of plasmid pMT101.; Plasmid pMT 101, encoding Cm$^R$ and Tc$^R$ and a temperature-sensitive replicon such that plasmid replication is blocked at the restrictive temperature (42° C.), is constructed by inserting the Cm$^R$ locus from pBR325 into pPM103, which encodes TcR and a temperature-sensitive replicon. By virtue of the temperature sensitive replicon, plasmid replication is blocked at the restrictive temperature of 42° C.

Cell survival therefore depends entirely on the ability of a second plasmid to complement the glyS null allele. This second plasmid is introduced by transformation at the permissive temperature and retained at the temperature that is restrictive for the first temperature-sensitive plasmid. The second plasmid contains specific glyS sequences to be tested.

Functional recA activity is required for the site specific recombination of linear DNA fragments. The recA+ phenotype must be converted to recA− to prevent recombination between plasmid-borne sequences and the chromosome. In the present example, it is not possible to inactivate recA simultaneously with the deletion of glyS by a double reciprocal recombination of a single linear DNA fragment. A two-step procedure is required in which the glyS deletion in TM101/MT901 is first created and a gene for a functionally deficient glycine tRNA synthetase, the recA 56 allele in *E. coli* GW554, moved into this strain by P1 transduction. The resulting temperature-sensitive ΔglyS recA strain is designated TM 102/pMT 901.

The glyS deletion in TM101/pMT901 was created as follows. Plasmid pTK101 contains a 10 kbp PstI fragment which encompasses glyS and several kbp of 5'-and 3'-adjoining sequences. The central 5 kbp HindIII fragment of the PstI segment encoding glyS was replaced with a 3.3 kbp HindIII fragment encoding Kan$^r$ from bacterial transposon Tn5. One microgram of the resulting plasmid, pMT300, was digested with EcoRI and NdeI at unique sites in the pBR322 portion of pMT300, and transformed into *E. coli* JC7623/pMT901. Selection for Kan$^r$ yielded approximately 70 transformants. These transformants were presumed to have the ΔglyS/Kan$^r$ allele and one of them was designated as TM101/pMT901. After the recA56 allele was moved by P1 transduction into TM101/pMT901 to produce TM102/pMT901, both ΔglyS and recA56 alleles were moved by P1 transduction from TM102/pM901 to a wild-type C600 strain to produce the ΔglyS/Kan$^r$ recA strain TM202/p901. Linkage of Kan$^r$ to xyl-5 in this strain was shown to be similar (90%) to that reported for linkage of glyS to xyl (80%). The genomic arrangement predicted for ΔglyS Kan$^r$ was also verified by Southern blot analysis.

Further details of this example are discussed in the patent application U.S. Ser. No. 833,920 filed Feb. 26, 1986 entitled "Construction and Application of Polyproteins" by Matthew J. Toth and Paul R. Schimmel and in "Internal Structural Features of *E. coli* Glycyl-tRNA Synthetase Examined by Subunit Polypeptide Chain Fusions" in *J. Biol. Chem.* 26115), 6643-6646 (1986).

As demonstrated, the glyS gene was not permanently deleted from the *E. coli* unless the recA gene was also deleted or inactivated. In the presence of recA functional activity, it appears that the first maintenance plasmid encoding the essential gene is integrated into the cell chromosome under the intense selection pressure created by the removal of the plasmid containing the temperature sensitive replicon by growing the organisms at an elevated temperature. In contrast to the first example requiring the "immediate" removal or inactivation of the recA gene, removal occurs simultaneously with deletion of the gene. In the present case, removal occurs over a period of one to two days. The exact time required is a function of a number of factors which may be determined by one of skill in the art. The selection pressure is a result of the interplay of the means available to maintain the system in the absence of the essential gene, the presence of extrachromosomal DNA in the cell which encodes the essential gene, the method used to remove or inactivate the recA gene, the conditions under which the cell is grown (or not grown, i.e., the status quo could be maintained indefinitely by freezing or lyophilization), and other factors known to those of reasonable skill in the art.

The P1 transduction was done under standard conditions, as described by J. Miller in *Experiments in Molecular Biology*, pages 201-205 (Cold Spring Harbor, New York, 19720. This took approximately two days to test. "Stressing" in the case of the glyS gene deletion was to raise the temperature to a level at which the maintenance plasmid could not replicate. Since only those organisms having a functional gene encoding glycine tRNA synthetase incorporated into the chromosome can survive, there is intense selection for recombination of the plasmid gene with the cell chromosome.

The linear fragments which are useful in the present invention can be constructed using methods known to those skilled in the art. Techniques including subtraction methods can be used to isolate the recA gene and flanking sequences (for example, using RecA− and RecA+ strains). Other sequences can be prepared using an oligonucleotide synthesizer since less than 125 to 150 nucleotides of homologous sequence on either side of the gene to be deleted are required for the double reciprocal recombination. The partial sequences for a number of recA genes and RecA proteins have been published (see, for example, *Mol.Gen.Genet.* 204, 161-165 (1986); T. Moris et al, *Proc.Natl.Acad.Sci. USA* 77, 313-317 (1980); A. Sancar et al, *Proc.Natl.Acad.Sci. USA* 77, 2611-2615 (1980)). In numerous other cases, the protein has been purified and could be sequenced or probes have been isolated which hybridize to either the 3' or 5' ends of the gene.

Modifications and variations of the present invention, a method and means for deleting a gene by double reciprocal recombination in combination with manipulations of recA in a variety of bacteria, will be obvious of those in the art from the foregoing detailed description of the invention. Such modifications and variations are intended to come within the scope of the appended claims.

I claim:

1. A method for deletion of a gene from a bacteria comprising:
   (a) constructing a linear DNA fragment wherein the fragment has sequences sufficiently homologous to regions on the cell chromosome flanking the gene to be deleted; to permit base pairing therebetween
   (b) placing a second gene whose expression results in a rapidly detectable phenotype between the hybridizing sequences in the DNA fragment;
   (c) introducing the linear DNA fragment into bacterial cells;
   (d) selecting for a double reciprocal recombination mediated by the RecA gene by culturing the cells containing the linear DNA under conditions wherein the phenotype encoded by the second nucleotide sequence is detected and cells with a double reciprocal recombination express the detectable phenotype; and
   (e) altering the cell strain phenotype from recA+ to recA− immediately after the linear DNA fragment is incorporated into the cell chromosome by introduction of a second linear DNA fragment containing sequences homologous to regions flanking the recA gene.

2. The method of claim 1 further comprising selecting the host bacterial strain from the group of bacteria consisting of Proteus, Erwinia, Shigella, Haemophilus, Streptococcus, Salmonella, Pseudomonas, Rhizobium, Agrobacterium, Vibrio, and Bacillus.

3. The method of claim 1 wherein the cell strain phenotype is altered from RecA+ to RecA− immediately by incorporating into the linear fragment containing the sequences flanking the gene to be deleted a sequence homologous to and deleting the RecA region.

4. The method of claim 1 wherein the cell strain phenotype is altered from RecA+ to RecA− by transduction of the second linear fragment into the cell strain immediately following the double reciprocal recombination deleting the gene.

5. The method of claim 1 wherein the cell strain phenotype is altered from RecA+ to RecA− immediately by mating the RecA+ strain with a second appropriate RecA− strain.

6. The method of claim 1 for deleting a gene for a first host protein, wherein the detectable phenotype for the gene deletion is the absence of the second protein in the host.

7. An isolated DNA fragment consisting essentially of between approximately 80 to 100 nucleotides homologous to nucleotide sequences located adjacent to the recA gene in bacteria, wherein binding between the nucleotide sequences and the isolated fragment results in deletion of the rec a gene.

8. The linear DNA fragment of claim 7 further comprising sequences encoding the recA gene.

9. The linear DNA fragment of claim 7 further comprising a gene encoding a detectable phenotype when expressed in a bacterial host.

10. A linear DNA fragment for deleting a gene from a bacterial chromosome consisting essentially of between approximately 80 to 100 nucleotides homologous to sequences 5' and 3' to the gene to be deleted and a gene selected from the group consisting of genes whose expression results in a detectable phenotype of temperature sensitivity, ultraviolet radiation sensitivity, auxotrophism for a sugar, auxotrophism for an amino acid, auxotrophism for a protein, auxotrophism for a nucleotide, and which encode for a specific cellular component detectable by chemical, radioactive, or immunological screening techniques, wherein binding between the nucleotide sequences and bacterial chromosome results in insertion of the selected gene in place of the gene to be deleted.

* * * * *